United States Patent [19]

Spinosa et al.

[11] Patent Number: 4,634,420

[45] Date of Patent: Jan. 6, 1987

[54] APPARATUS AND METHOD FOR REMOVING TISSUE MASS FROM AN ORGANISM

[75] Inventors: Joseph D. Spinosa, Woodbury; Dominic J. Spinosa, Wantagh, both of N.Y.

[73] Assignee: United Sonics Incorporated, Hauppauge, N.Y.

[21] Appl. No.: 662,843

[22] Filed: Oct. 31, 1984

[51] Int. Cl.⁴ .............................................. A61B 17/20
[52] U.S. Cl. ...................................... 604/22; 128/305; 433/119
[58] Field of Search ............... 604/43, 44, 167, 169, 604/22, 282; 128/24 A, 305; 433/119

[56] References Cited

U.S. PATENT DOCUMENTS

| | | |
|---|---|---|
| 3,498,286 | 3/1970 | Polanyi et al. .................. 604/282 |
| 3,589,363 | 6/1971 | Banko et al. ...................... 604/22 |
| 3,776,238 | 12/1973 | Peyman et al. . |
| 3,857,387 | 12/1974 | Shock . |
| 3,875,938 | 4/1975 | Mellor .............................. 604/169 |
| 3,942,519 | 3/1976 | Shock . |
| 3,952,732 | 4/1976 | Shock . |
| 3,990,452 | 11/1976 | Murry et al. . |
| 4,000,739 | 1/1977 | Stevens ............................ 604/167 |
| 4,014,333 | 3/1977 | McIntyre ......................... 604/167 |
| 4,096,860 | 7/1978 | McLaughlin ..................... 604/44 |
| 4,099,529 | 7/1978 | Peyman ........................... 128/305 |
| 4,425,115 | 1/1984 | Wuchinich ........................ 604/22 |
| 4,428,748 | 1/1984 | Peyman et al. ................. 433/119 |
| 4,493,694 | 1/1985 | Wuchinich . |
| 4,493,698 | 1/1985 | Wang et al. . |

OTHER PUBLICATIONS

*Popular Mechanics,* "Ultrasound–Medical Marvel", Jul. 1979, pp. 54–55.

Primary Examiner—C. Fred Rosenbaum
Assistant Examiner—Jerome R. Smith, Jr.
Attorney, Agent, or Firm—Hoffmann, Dilworth, Barrese & Baron

[57] ABSTRACT

An apparatus and method useful for the removal of a mass of tissue from an animal which includes an elongated instrument, such as a needle, with a sheath device having a sleeve for treatment fluid delivery at the area of operation. The needle can be vibrated at ultrasonic frequency, preferably in the lateral direction, and treatment fluid, along with reduced pieces of tissue mass, can be removed from the area of treatment by means of aspiration through a conduit in the needle.

53 Claims, 10 Drawing Figures

APPARATUS AND METHOD FOR REMOVING TISSUE MASS FROM AN ORGANISM

BACKGROUND OF THE INVENTION

The present invention relates to treatment of biological organisms which includes selective removal of tissue mass therefrom by use of vibrational forces, such as ultrasonic vibrational forces, and in particular, to an apparatus and method for reducing and removing tissue mass from the organism using a treatment fluid.

The principles of the present invention are broadly applicable to the removal of layers of tissue mass, and are particularly adapted for use in conjunction with removal of organic tissue such as that found in the eye.

It has been known in the art of removing unwanted tissue mass from animals, such as humans, to effect such removal by use of ultrasonic energy. Specifically, in the art relating to removal of cataracts, it is known to use a tip in the form of a hollow needle which is subjected to ultrasonic vibration, and is surrounded by a plastic tube which is not subjected to vibration. This combined tube and needle can be inserted into the anterior chamber of the eye through a small incision, while provision is made for maintaining hydrodynamic flow both in the area between the needle and the tube and within the interior of the vibrating tube. It is of the greatest importance in prior art procedures that a proper balance be established between the two flows in order to prevent an excessive build up of pressure in the anterior chamber or a reduction in pressure which could cause a collapse of the anterior chamber.

In order to insure maintenance of this sensitive and delicate balance, practitioners have found it necessary to use a very complex electro-hydraulic means having a series of failsafe characteristics incorporated therein. Moreover, problems can be encountered in insuring that every particle of dispersed cataract material is aspirated before making some unwanted orbit in the anterior chamber. In other words, for example, if a population of 100,000 small particles were created by ultrasonic microchopping, these particles are created in the presence of an inflowing stream of liquid combined with an adjacent rapidly outflowing stream of liquid. The hydrodynamic circulation in the anterior chamber, or in the posterior chamber if that is the area of operation, under these circumstances would allow for the movement in the anterior chamber of those few particles which might accidently escape from time to time during the operation.

In the case of hard cataracts such particles could very well have an abrasive character if they were to slide past in contact with the walls of the chamber. In the case of the endothelium of the cornea which forms a part of this chamber, there is extreme sensitivity to any such abrasion and must be avoided at all costs.

Briefly, the procedure known today, such as disclosed in U.S. Pat. No. 3,589,363, includes a process for removal of cataracts by emulsifying the the lens with an ultrasonic probe requiring aspiration of the emulsified material. Since aspiration is a required aspect of the procedure, it is necessary to have complex electronic and hydraulic equipment for delicate control of inflow and outflow in the eye. This complex equipment requires a trained technician to control and monitor such equipment, especially since the aspiration requires very careful manipulation of the tip by the surgeon in order to prevent aspirating other than cataract material.

Other disclosures such as U.S. Pat. No. 3,990,452, U.S. Pat. No. 3,776,238, and U.S. Pat. No. 4,099,529, describe instruments for ophthalmic surgery which consists of a hollow needle with internal moveable hollow cylinder, capable of cutting tissue by reciprocation, and in which an opening has been formed in the outer needle so that material can be engaged by the inner plunger so as to be sheared. See also U.S. Pat. No. 4,428,748 which discloses combined ultrasonic emulsifier and mechanical cutter for surgery including an outer tube means and an inner tube means mounted by reciprocal driving in order to shear eye tissue.

Another method of removing cataract material from the eye is disclosed in a series of patents which describe ultrasonic instrumentation and a method for removal of unwanted tissue material from an animal by use of cryogenic application and ultrasonic vibration in combination with a flow of liquid and cataract mass from an incision in the eye structure. See U.S. Pat. Nos. 3,857,387; 3,942,519; 3,952,732 to Shock. This method, however, suffers from certain procedural and instrumentative drawbacks, such as indiscriminate and uncontrolled emission of fluid from the eye structure. This condition detracts from surgical procedure in that it provides a continuous flow of fluid which creates a sloppy surgical work area, and does not insure complete reduced-mass removal.

It is, therefore, an object of the present invention to provide an improved apparatus and method for removing a mass of tissue from an animal, such as a human.

Another object of the invention is to provide an improve apparatus and method for removing cataracts.

A further object of the present invention is to provide an apparatus and method for selectively micro-chopping and removing layers of living organic tissue from a biological organism.

Another object of the invention is to provide an apparatus and method for the removal of living organic tissue from a cataract in a rapid manner and with little or no mess created by use of treatment fluids. A further object of the invention is to provide a hydrodynamically balanced fluid flow to the treatment area. Other objects and advantages of the present invention will become apparent as the disclosure proceeds.

SUMMARY OF THE INVENTION

The present invention is an apparatus and method for removal of organic tissue from animal, for example, humans, which includes an elongated vibratory instrument, such as a needle, and a sheath device for use with such instrument. The sheath device has a sleeve which has a length sufficient to extend substantially the length of the elongated instrument and which has a wall having a transverse cross-section with the inside perimeter greater than the outside perimeter of a transverse cross-section of the instrument so that fluid introduced to the sleeve means passes between the instrument and the sleeve means. The sheath device also includes a fluid delivery/withdrawal means connected for fluid communication with the sleeve means, and the fluid delivery/withdrawal means has an external port for introducing or withdrawing fluid. The sheath also includes a sealing means which fits cooperatively with the elongated instrument to prevent passage of fluid from the non-operative end of the instrument so that the sheath is capable of being sealingly fitted to the instrument, and so that treatment fluid continuously supplied to the sheath device is maintained at the operative end of the instrument substantially in the absence of interruption in the flow. It is contemplated that the elongated instrument can be a needle which is vibrated in operation, such as between from about 5,000 cycles per second to about 50,000 cycles per second, and preferably at about 27,000 cycles per second. It is important to the present invention that the needle can be vibrated laterally so that the operative end makes essentially an eliptical pattern.

The needle which can be used as the vibratory instrument includes an elongated barrel means having an operative end and a non-operative end, and is provided with a conduit extending the length thereof with an inlet port at the operative end. The needle also includes a base means provided at the non-operative end of the barrel means in which a connecting conduit is present therethrough so that fluid communication can be made between the barrel conduit and an outlet port at the non-operative end of the base means. The base means also has a connecting means for connecting the needle to a source of vibratory motion. The needle includes a sealing means for sealingly mounting a fluid sheath means on the needle. In the preferred embodiment the needle can be made of a titanium alloy.

It is contemplated that the barrel of the needle can have a circular transverse cross-section with an exterior circumference having a diameter of from about 0.031 to about 0.044 inches, preferably from about 0.035 to about 0.042 and can have a conduit with a circular transverse cross-section having a diameter of from about 0.024 to about 0.042 inches, and preferably from about 0.028 to about 0.035 inches.

In one embodiment of the present invention the operative end of the barrel is beveled to form an operative edge and the inlet port which, in this case, is the opening formed in the beveled end by the conduit. Another embodiment of the invention includes an end wall on the operative end of the barrel by which the conduit is closed, and an inlet port provided by an opening in the side of the barrel proximal to the end wall. In this latter case the inlet port can have an orifice of between about 0.020 and about 0.070 millimeters in diameter, preferably from about 0.025 to about 0.055 mm, and most preferably is about 0.3 millimeters in diameter. Furthermore with regard to this embodiment, since the surgeon or operator can use this needle for removing stringy vitreous material, it is important, therefore, that the end of the barrel does not extend too far past the operating inlet port in order to prevent inadvertent damage to the interior surface of the eye. Accordingly, it has been found that the distance between the outer surface of the end wall and the center line of the orifice should be not more than about 0.035 inches.

A further alternative of this latter embodiment of the needle of the present invention has an end wall on the operative end and an inlet port provided by an opening in the end wall. In this embodiment the inlet port is an orifice between about 0.20 and about 0.70 millimiters in diameter, and preferably from about 0.025 to about 0.055 mm, while the preferable size includes an orifice having a diameter of about 0.03 millimiters.

In a preferred mode of the present invention, the connecting means on the base of the needle can be a threaded portion for screwing the base into the source of vibratory motion. Furthermore, the barrel can include a means for rotating the needle such as flattened areas on the outer circumferential surface of the barrel whereby rotating force can be applied to the needle.

A preferred embodiment of the invention also includes sealing means on the needle and the sheath which can be an annular ring extending from the surface of the needle base on the interior surface of the sheath for sealing fit into an annular groove provided on the interior surface of the sheath means or on the exterior surface of the base. In this embodiment the annular ring can have a dome cross-section with a width of from about 0.007 to about 0.025 inches, and preferably from about 0.012 to about 0.018 inches, and a cross-sectional height from the surface of the base of the needle or from the surface of the sheath of from about 0.010 to about 0.030 inches, and preferably from about 0.014 to about 0.020 inches, while the annular groove can have a cross-sectional width of from about 0.006 to about 0.030 inches, and preferably form about 0.014 to about 0.022 inches, and a cross-sectional depth of from about 0.006 to about 0.30 inches and preferably from about 0.012 to about 0.024 inches. Also in this embodiment, the diameter of the circle defined by the inner circumference of the annular ring when it is on the sheath can be from about 0.070 to about 0.130 inches, and is preferably from about 0.090 to about 0.100 inches, and the diameter of the circle defined by the bottom of the groove when formed in the base can be from about 0.040 to about 0.120 inches, and is preferably from about 0.075 to about 0.080 inches so that the groove can be sealingly secured over the ring.

Similarly, when the annular ring is formed on the base, the diameter of the circle defined by the outer surface of the ring can be from about 0.040 to about 0.120 inches, and is preferably from about 0.090 to about 0.100 inches, whereas the diameter of the circle defined by the bottom of the groove when it is formed in the interior surface of the sheath can be from about 0.070 to about 0.130 inches, and is preferably from about 0.75 to about 0.080 inches.

As indicated before, an alternative of this embodiment includes a sealing means which is a continuous annular groove formed on the outside wall of the needle base, such as by raised flanges, for sealing fit of an annular ring provided on the interior surface of the sheath means. In this case the annular groove can have a cross-sectional width and a cross-sectional depth as set forth before. The annular ring also can have a dome-shaped cross-section with a width and a height as previously indicated.

Referring now to a sheath device which can be used in combination with an elongated instrument having an operative end and a fluid supply, the present invention contemplates a sheath device having a sleeve means with a wall thickness of from about 0.001 to about 0.009 inches and in which the sleeve means has a transverse cross-section with an interior from about 0.002 to about 0.016 inches greater than the exterior perimeter of the transverse cross-section of the instrument, and preferably from about 0.004 to about 0.006 inches. Preferably, the sleeve means as a circular transverse cross-section with an inside diameter of about 0.048 to about 0.068 inches, and an outside diameter of from about 0.060 to about 0.080 inches. In the most preferred embodiment of the invention, the wall of the sleeve means is tapered at the end which is proximal the operative end of the instrument, and there is provided at least one diffusion orifice in the same end so that fluid provided thereto is diffused from direct exit through the end of the sleeve.

In the most preferred embodiment there are two openings through the wall of the sleeve means at a position proximal the operative end of the instrument, such openings being oposite each other.

In order to achieve such thin-walled sleeve means, it has been found that a reinforcement means can be provided which prevents the wall from longitudnal collapse in the presence of compressive force, such as insertion through a small incision in an eye surface. Specifically, the present invention contemplates the use of at least one rib means extending longitudinally along the wall of the sleeve means, and preferably includes four rib means advantageously spaced around the perimeter of the wall. It is preferred that the rib means be placed on the interior of the wall of the sleeve means and that such ribs have a dome cross-section with a width of from about 0.006 to about 0.012 inches and a height from the interior surface of the sleeve means of from about 0.002 to about 0.006 inches.

In the most preferred embodiment of the present invention the sheath means further includes a fluid reservoir means having a dimension sufficient to hold a volume of fluid at least equal to the volume of the fluid held between the instrument and the sleeve means so that a supply of fluid provided by gravity flow is continuously maintained through the sleeve means. Such reservoir means can be an extension of the sleeve means having at least one, and in a preferred embodiment two, enlarged transverse cross-sectional areas and a length sufficient to hold the volume of fluid described above. Preferably the transverse cross-section of the reservoir is substantially circular in shape and, when there are two cross-sectional dimensions, the first one adjacent the barrel conduit can have diameter of from about 0.130 to about 0.145 inches and a length of from about 0.055 to about 0.075 inches while the second cross-section can be from about 0.055 to about 0.120 inches in diameter for a length of from about 0.008 to about 0.145 inches.

The sheath means of the present invention also includes fluid delivery/withdrawal means which can have a body means at the non-operative end of the sleeve means which in turn has a fluid delivery/withdrawal bore extending from an external port and is in fluid communication with either the reservoir or the sleeve means. Furthermore, an attachment means can be provided at the external port of the fluid delivery withdrawal bore for connecting a fluid passage tube. The bore referred to above can meet reservoir or the sleeve means at an angle of from about 45 to about 90 degrees and preferably meets the sleeve means at an angle of about 60 degrees. The bore can be cylindrical and have a transverse cross-section with a diameter of from about 0.054 to about 0.062 inches, while the attachment means can be an enlargement in the cross-section dimension of the bore so that a fluid passage tube can be inserted therein. The cross-section of this enlargement can have a diameter of from about 0.125 to about 0.142 inches. The present invention can include a fluid passage tube which can be a cylindrical infusion tube made of, for example, polyethylene or silicone rubber, and having a cross-section with an outer diameter of from about 0.125 to about 0.142 inches. Depending on the nature of the application, the fluid passage tube can be permanently secured to the attachment means or can be removably attached thereto, such as by friction fit. When the fluid passage tube is a solid-walled tube, the angle at which the bore meets the sleeve is preferably from about 58 to about 62 degress, and most preferably about 60 degress, so that the tube can be gently curved at a point proximal to its attachment to the bore.

In another embodiment when the angle at which the bore meets the barrel conduit is 90 degrees, it is believed that the fluid passage tube should have a substantially serrated outer wall surface profile at a point proximal its attachment to the bore so that the tube can be bent at that point with reduced outer surface tension on the tube and reduced deformity of the interior passage of the tube. In this latter embodiment the wall of the fluid delivery tube can be of from about 0.024 to about 0.030 inches thick and the depth of the depressions of the serrations can be from about 0.010 to about 0.017 inches. The apexes of said serrations can be either peaks or truncated peaks. Furthermore, in this embodiment, the pitch of the seration can be from about 0.025 to about 0.035 inches.

The preferred method contemplates vibrating the instrument in the lateral direction, and providing the treatment fluid at the area of reduction by the pressure of gravity.

In all cases the sheath memeber can be made from a synthetic polymeric material so that it is easy to fabricate and can be thrown away after use.

The present invention is also directed to a method for removing a mass of tissue from an animal, such as a human, with a vibratory instrument having an output end which includes reducing the size of the mass by engaging the output end against the mass and ultra-sonically vibrating the output end. Treatment fluid can be continuously provided under low pressure at the area of reduction without an interruption in flow, and treatment fluid along with reduced tissue mass can be removed without substantial depletion of the amount of treatment fluid at the area of tissue reduction. This method is especially effective for removing cataract tissue mass from the eye.

As a result of the present invention, a highly effective vibratory needle and treatment fluid sheath means can be provided in which treatment fluid can be supplied to the area of operation with the gentle pressure provided by gravity flow without an interruption in said flow or area of negative pressure which could cause collapse of the eye structure, whether it be the anterior or posterior section of the eye. Furthermore, the present invention provides the treatment fluid at the area of operation in the absence of a directed stream which could obfuscate or unduly disperse fragments which must be aspirated from the eye.

Another advantage realized by the present invention is a inexpensive device for use in cataract removal wherein treatment fluid delivery is used which does not result in a sloppy work area or "wet lap" to the operating surgeon, and which can be thrown away after a single use.

The laterally vibrating needle of the present invention can be readily applied to the unwanted tissue mass without "plugging" which can result from reciprocating action needles used previously for this purpose. Additional embodiments of the needles of the present invention provide unique "clean up" instruments for use in conjunction with cataract removal, which have heretofore not been known in the art.

As a further result of the present invention a very small incision can be made in order to insert the highly effective device, since the sleeve wall can be made to be very thin with the help of reinforcement longitudnal ribs. This feature prevents "skinning back" or an "accordian effect." Such reinforcement features also prevent "pinching off" of irigation flow when the incision may be very small. Another advantage which the ribbed sleeve provides is that it is prevented from contacting the vibrating needle, thereby dampening the vibratory motion.

The new annular seal feature of the present invention, as mentioned before, provides a fluid reservoir for maintaining the amount of fluid in the sleeve, while at the same time preventing escape of treatment fluid into the surgical area and onto the operator. Furthermore, the annular seal also restricts pulling of the sheath means from the vibratory instrument so that the operating surgeon can rely on a compact unitary combination device throughout the operation.

For a better understanding of the present invention, together with other and further objects, reference is made to the following description, taken in conjunction with the accompanying drawings, and its scope will be pointed out in the appended claims.

BRIEF DESCRIPTION OF THE DRAWINGS

Preferred embodiments of the invention have been chosen for purposes of illustration and description and are shown in the accompanying drawings, wherein.

DETAILED DESCRIPTION OF THE INVENTION

Description of the Surgical Procedure

The present invention is particularly useful in the removal of unwanted tissue mass from the eye and for use in cleaning such reduced mass from the eye structure. In the surgical procedure for which the present invention has been designed the patient can be given a local anesthetic which consists of, for example, a lid block and a retrobulbar injection. This local anesthetic is all that is generally required for conventional cataract removal procedures; but in the past it has been known to use a general anesthetic for such procedures in order to prevent movement of the eye during operating procedure.

After the anesthetic has been administered, a small limbal or fornix based conjunctival flap is performed. Then, a small limbal incision, e.g., less than about six millimeters, and preferably about three to four millimeters, can be made into the anterior chamber of the eye if that is the area on which the operation is to be performed. In the past, in at least one procedure, the aqueous was removed from the anterior chamber while a small amount of air was inserted therein, and a small cystotome would be inserted through the incision to remove the anterior capsule of the lens. However, with the present invention it is not contemplated that the aqueous must be removed. In the event the anterior capsule cannot be completely withdrawn by the cystotome, a small pair of capsule forceps can be inserted to complete the removal.

At this point in the procedure, a thin-walled, approximately 19 or 20 gage metallic needle, preferably titanium, which can be vibrated with ultrasonic energy, is inserted into the anterior chamber through the incision. As a result of the very thin-walled sheath which can be provided in the present invention, the incision need not be enlarged as has been known in the past when such needle covering devices have been used. Prior to the insertion of the needle, a slow drip of physiological saline is allowed to flow continuously through the tube into the sleeve means. This flow of fluid through the needle is accomplished merely by providing a gravity feed flow from, for example, an intravenous pole arrangement.

One of the greatest advantages of the present invention is the simplicity of using merely the pressure of gravity, as well as the low pressure flow of the gravity feed system which is more than adequate to permit the inflow of treatment fluid, and consequently, the maintenance of the anterior chamber and removal of fragmented material, without the need for complex irrigation and aspiration controls. In view of this fact an aspiration system can be continuously connected for operation, and it is unnecessary to rely on continuous drainage of lavage fluid to remove of the reduced cataract mass, which results in a sloppy work area, as is disclosed in U.S. Pat. Nos. 3,952,732; 3,942,519; and 3,857,387.

Having positioned the needle to the cataract while viewing the needle and anterial chamber area through an operating microscope and with the flow being in proper adjustment, the tip is ultrasonically energized for a short period of time. In the case of the present invention, the vibration is in a lateral direction thereby producing an essentially elliptical tip path. This ultrasonic energization fragments the material immediately adjacent to the tip. The period during which the tip is energized may vary anywhere from approximately a millisecond to a second, depending on the speed of foot movement in the case of a foot switch which can be provided for the operating surgeon. The surgeon selects the interval of energization to allow complete and perfect control of the operative procedure.

The mass of material forming the cataract to be removed is initially broken into a plurality of fragmented submasses or major sections which can thereafter be removed in their entirety or further fragmented into a pluarlity of particle size masses such that it can exit the work area through the aspiration conduit provided in the needle. During the surgical procedure, the surgeon can initially cross drill or bore a pluarlity of aperatures in the cataract to create a tunneling effect and these cross bores or apertures are formed by vibrating the ultrasonic member such that a plurality of submasses are formed during this aspect of the surgical procedure. These submasses are thereafter individually either reduced in size or of an initial size to permit their exiting through the aspiration conduit provided in the needle. In softer. cataracts only a small volume of the cataract need be ultrasonically fragmented. This allows a remainder to deform its shape due to the slight hydrostatic pressure differential, and the entire cataract will in a sense flow itself out through the orifice.

Accordingly, the tip or output edge of the needle-like tool member can be positioned in engagement with the immediate portion of the cataract to be removed, prior to ultrasonically energizing the tip of the needle tool member. Upon energization of the tip of the tool member, a portion of the cataract in surrounding relation thereto is fragmented and the size of the fragmented section is a function of hardness and nature of a cataract material; for example, the fragments may range from practically invisibility to section of millimeter dimensions. These fragments, depending on their size, are lavaged by the continuous stream of irrigation fluid previously described which is provided to the sheath means around the vibrating needle. This product engagment energization tip is repeated until such time as the entire catarac is fragmented and removed from the incision by aspiration. The use of the additional embodiments of the needle tool are ideally suited for removal of reduced cataract mass, without fear of incurring injury to any other parts of the eye.

Detailed Description of the Apparatus

Figures 1, 1A:
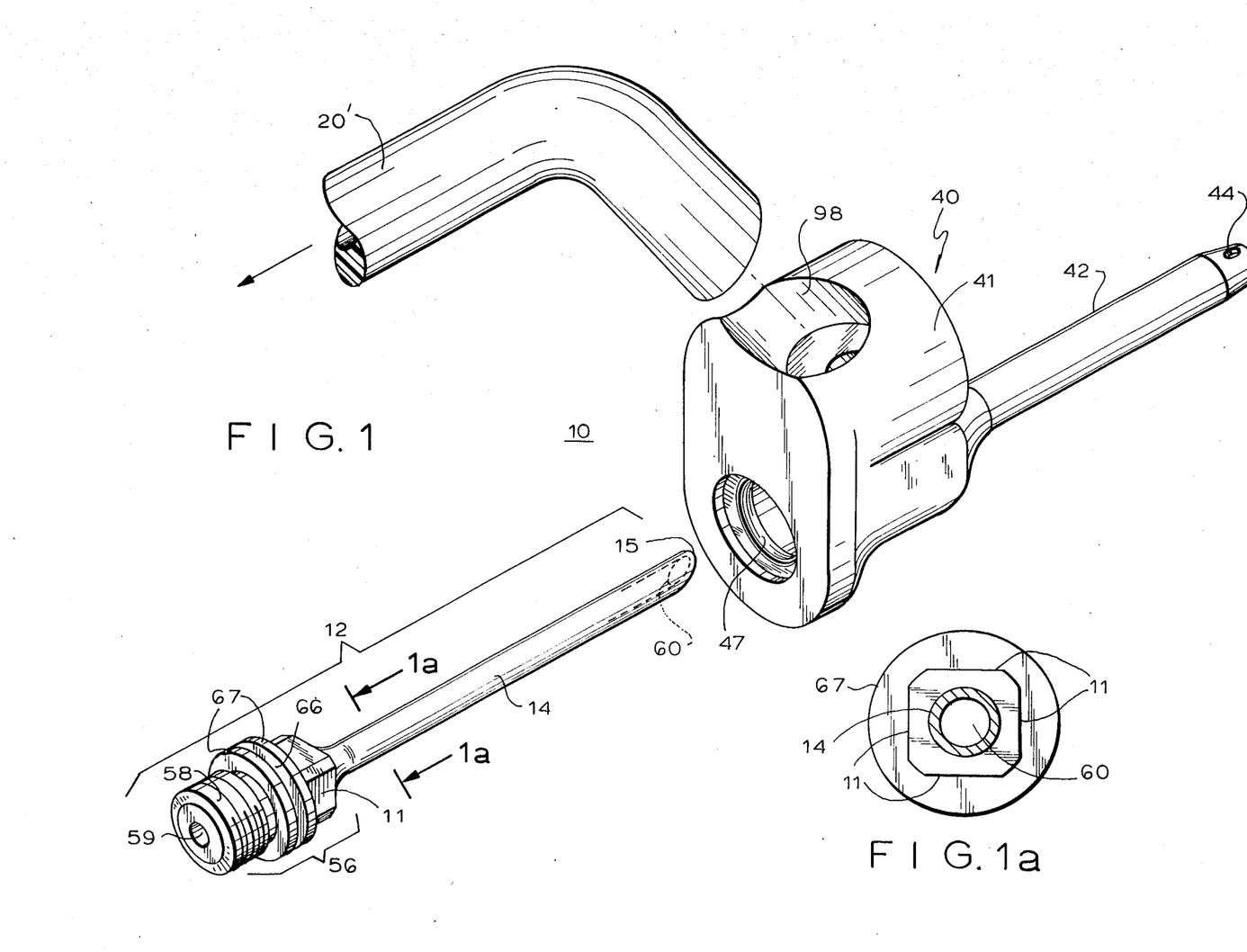
FIG. 1 is an exploded isometric view of a combination apparatus of the present invention.
FIG. 1a shows one embodiment of a needle cross section wherein there is provided a means for applying a rotating force to facilitate screwing the needle into a source of vibrating motion.
Figure 8:
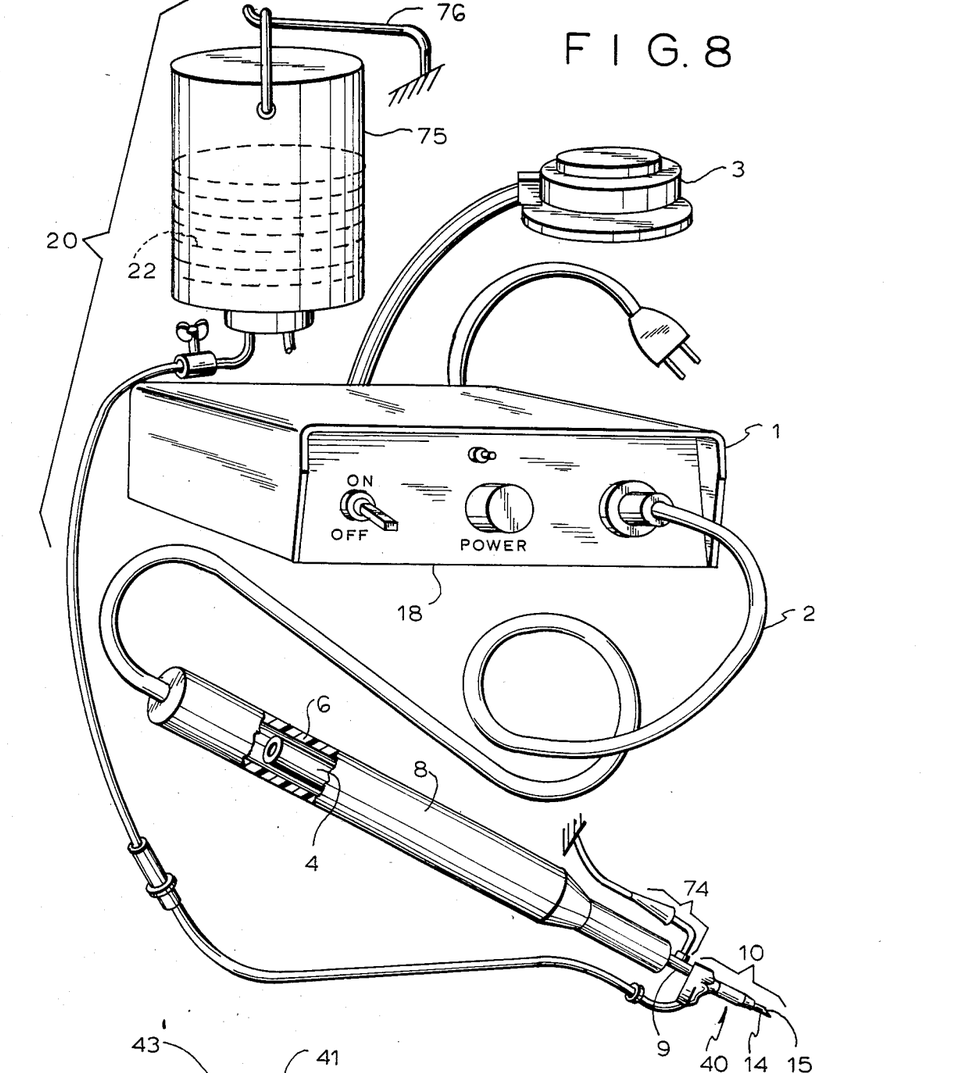
FIG. 8 depicts an overall operating system in accordance with the present invention.

Referring to the drawings in detail, it will be seen that the combined apparatus 10 for ultrasoncially removing tissue mass, such as a cataract from an animal may include an elongated instrument, such as a needle 12, for effecting the necessary high frequency vibrations of a probe or barrel 14 which can have a relatively sharp output edge or tip 15 in one embodiment of the invention. Operatively associated with the needle 12 is a generating means 18 for powering same and a fluid supply mean 20 for providing fluid 22 at the operative site. A source of vibratory motion which can be in the form of a handpiece adapted for being hand-held can include a tubular housing 6 with an ultrasonic motor or transducer 4 being contained therein and having an output end of stem 9 of the motor 4 extending axially beyond the front end of the housing 6 and to which the needle 12 can be coupled.

In the present invention the ultrasonic motor 4 is energized by the generator which can be contained in a cabinet 1 with a power cable 2 connecting the two together. The generator is an oscillator adapted to produce electrical energy having an ultrasonic frequency and containing a convenient shut off and on switch as well as an actuating foot pedal 3 for use by the operating surgeon.

The ultrasonic motor 4 may be one of a variety of electromechanical types such as piezoelectric or magnetostrictive. The ultrasonic motor is designed to operate at a desired frequency generally in the range of 5,000 cycles per second to 50,000 cycles per second but preferably, in the case of the present invention, in the range of about 27,000 cycles per second and the front output end is adapted to receive the working needle and vibrate such needle in the lateral direction rather than the reciprocal direction as is commonly known in the art. This lateral vibratory motion generally produces an eliptical path at the tip of the operating needle, and prevents unwanted plugging of the needle means aspiration conduit as well as giving the operator a higher degree of control over the area receiving ultra-sonic vibrations.

In the past transducers for such ultrasonic motors have been longitudnally dimensioned so as to have lengths which are whole multiples of half wavelengths of the waves generated therein such that the exterior working end of the ultrasonic motor would be a longitudnal loop of motion. While in the past it has been known to convert this longitudinal motion into lateral motion by use of an angularly fitted needle means, the present invention includes a transducer which provides lateral vibratory motion without the use of an angularly fitted needle. The amplitude of the vibration is generally in the range of 0.0001 to 0.010 and the hyper accelerations exceed 1,000 g at the tool tip 15. The design of the output end of the motor 4 and the tool tip 15 may be designed to either magnify or reduce the amplitude of the vibrations received from the ultrasonic motor 4.

As indicated before, the tool 14 may be a needle-like member having a base 56 with a threaded portion 58 which is adapted to connect with complementary threads in the output end 9 of the handpiece 8 and in the present invention, has an axially extending conduit 60 extending from the opening at the front end to the rear thereof to meet with a connecting conduit 59 formed in the base 56 which is in fluid communication with conduit 60. In this way a fluid is permitted to enter the front of the needle 14 and pass therethrough as hereinafter explained in detail. The base 56 can also be provided with a sealing means such as a continuous groove 66 or a continuous angular rib 68 which can be sealingly coperatively fit with the sheath means 40. Referring to FIG. 1a, the needle 12 can also be formed with a flattened outer surface 11 adjacent annular flanges 67, which form grove 66, to facilitate application of rotational force to the needle.

The needle 12 has integrally formed therewith a barrel portion 14 and a bore 60 extending axially therethrough to provide fluid passage. The operative tip 15 is preferably formed of an extremely hard, sterilizable material, such as titanium, and for most surgical applications is made of extremely small dimension. Since this is the only portion of the instrument that is brought into contact with the tissue to be broken apart and removed, it will be evident that only a very short incision need to be made in the outer surface to permit access of the tip. Preferably the outer diameter of the transverse section of the barrel portion 14 can be in the range of 0.031 inches to about 0.044 inches but is preferably in a range of from about 0.035 inches to about 0.042 inches. The conduit 60 should be of a size to permit continuous flow of fluid along with reduced tissue mass therethrough, e.g., from about 0.024 to about 0.042 inches, and preferably from about 0.028 to about 0.035 inches.

Figures 2, 3:
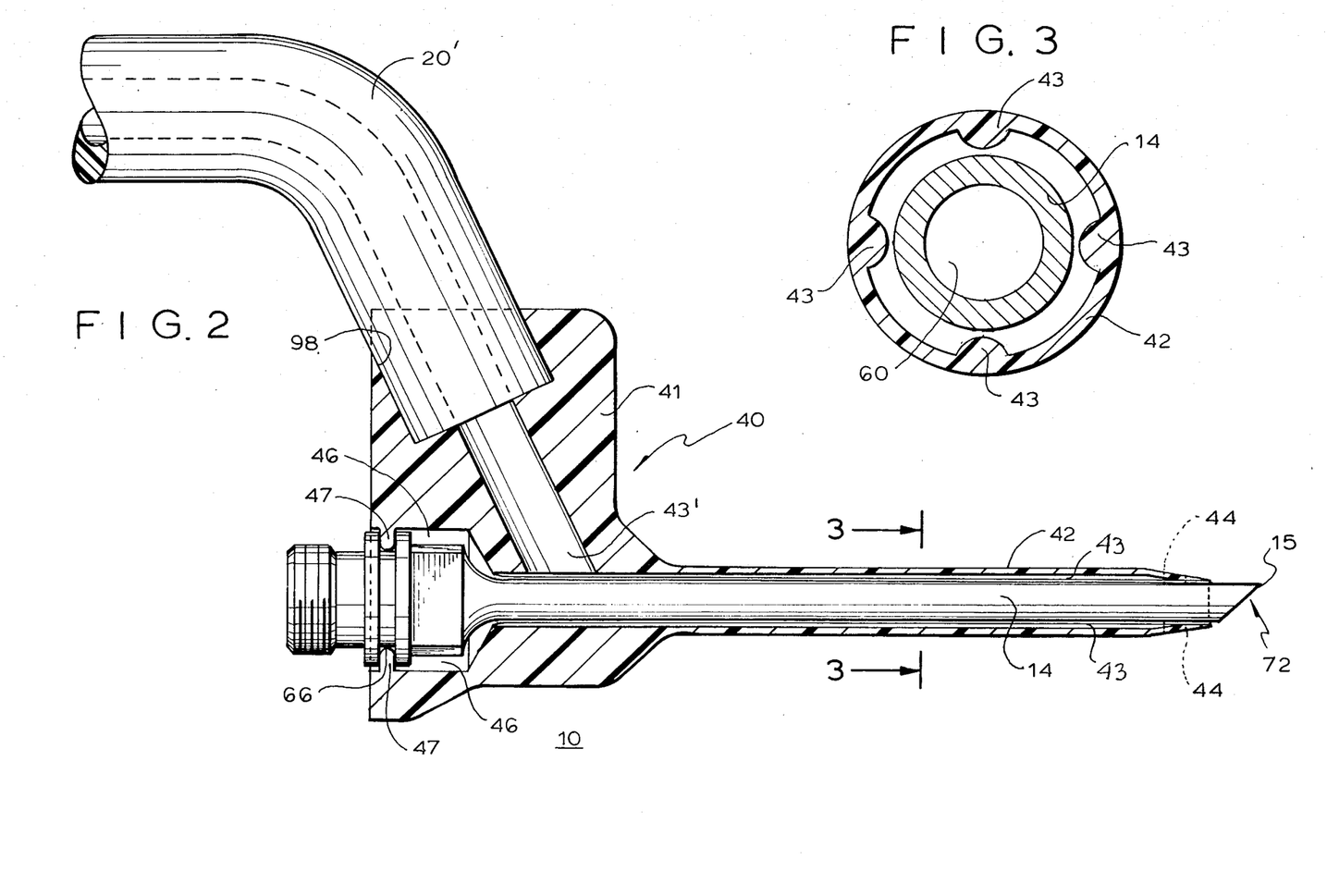
FIG. 2 depicts an assembly of the needle and sleeve of the present invention in an elevated side view with the sheath means in section.
FIG. 3 is a transverse section of the combination sleeve and needle as shown in FIG. 2.
Figure 4:
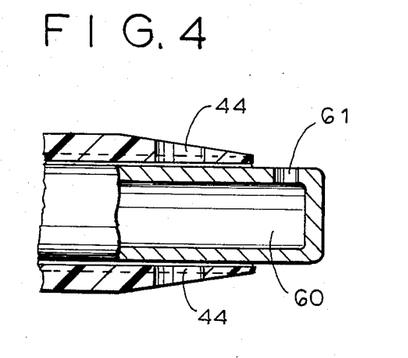
FIGS. 4 and 5 show additional embodiments of a vibrating needle in accordance with the present invention.
Figure 5:
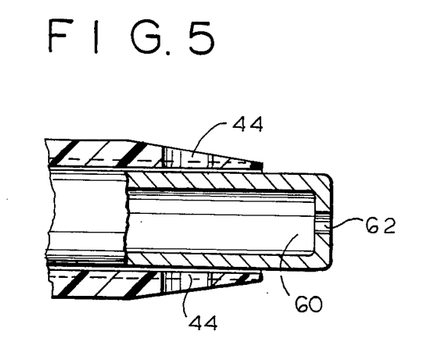

As seen in FIG. 2, an acute tapered angle 72 is provided in one embodiment to leave a relatively sharp, rounded edge 15. The shape, length, and dimensions of the tool member may vary depending on the type of mass or cataract to be removed. Alternative embodiments shown in FIGS. 4 and 5 show a tissue mass removal neeedle 14 whereby the end of the needle is a flat end wall having a small orifice either adjacent the end wall on the side, as seen as opening 61 in FIG. 4, or through the end wall, seen as opening 62 in FIG. 5.

While in operation, the conduit 59 through the base can be connected to a fluid passage tube system 74 which, in turn, is connected to a source of negative pressure such as an aspiration reservoir, whereby fluid can be aspirated from the area of treatment through the bore 60 and out of the eye. When using the tissue removal needles shown in FIGS. 4 and 5, the negative pressure can be applied to, for example, vitreous strands of unwanted tissue mass and the operator can momentarily energize the vibratory tip to disconnect such stringy mass from the eye structure. The flat end wall is advantageous in that it does not extend beyond the sight of the operator and is therefore less likely to do damage to any part of the eye structure. To this end it has been found that when the orifice is on the side of the barrel wall as shown in FIG. 4, the distance between the end wall and the center line of the orifice should be as close as possible, and preferably not more than about 0.035 inches.

Referring now to the sheath means in the combination of the present invention, there can be seen in FIGS. 1 and 2 a sheath 40 having a sleeve 42, which is of a length substantially the same length of the operating barrel 14. In one embodiment it is known that the needle should extend from about 1/16 to about ¼ inches beyond the sleeve of the attached sheath. Furthermore, the sleeve of the present invention is preferably a very thin-walled sleeve having a wall thickness of from about 0.001 to about 0.009 inches, and preferably about 0.004 inches thick and in this case, is preferably reinforced by rib means 43 which extend longitudinally the length of the sleeve. A further feature of the sleeve in accordance with the present invention includes openings 44 at the end of the sleeve, which can be tapered, so that-treatment fluid provided at such end can be diffused outwardly rather than being directed straight onto the work site from between the sleeve and the barrel of the needle. Preferably there are four ribs 43 provided around the interior circumference of the sleeve in order to prevent collapse or skinning back in response to compressive force applied thereto when the combination apparatus 10 is inserted into the eye. These ribs can be have a dome cross-section and having a dimension of from about 0.006 to about 0.012 inches wide and a height of from about 0.002 to about 0.006 inches.

In further reference to the sheath, there can be provided a reservoir 46 which can be an extension of the sleeve at the non operative end and have an enlarged cross-section of from about 0.130 to about 0.145 inches in diameter and a length of from about 0.005 to about 0.075 inches so that a reservoir of treatment fluid can be continually provided to the sleeve as treatment fluid is aspirated from the operative site through the needle.

Figure 2A:
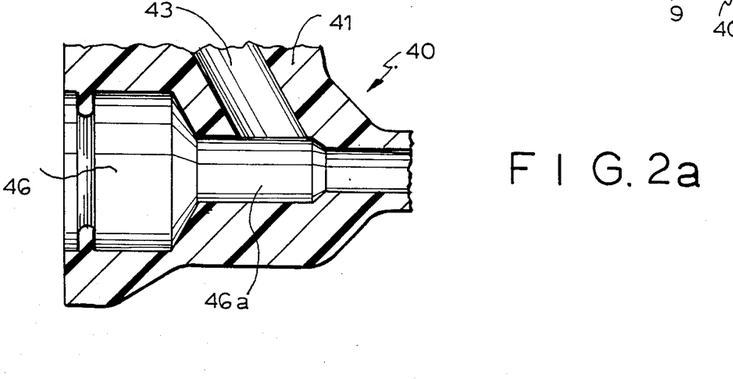
FIG. 2a shows in partial section an alternative embodiment of the sheath means wherein the reservoir has two enlarged cross-sectional dimensions.

In FIG. 2a an alternate embodiment is shown in which the sheath means has a reservoir with two enlarged cross-sectional dimensions. The diameter of the largest enlargement can be the same as indicated above while the smaller dimensioned enlargement can have a diameter of from about 0.055 to about 0.120 inches and a length of from about 0.080 to about 0.145 inches.

Figure 6:
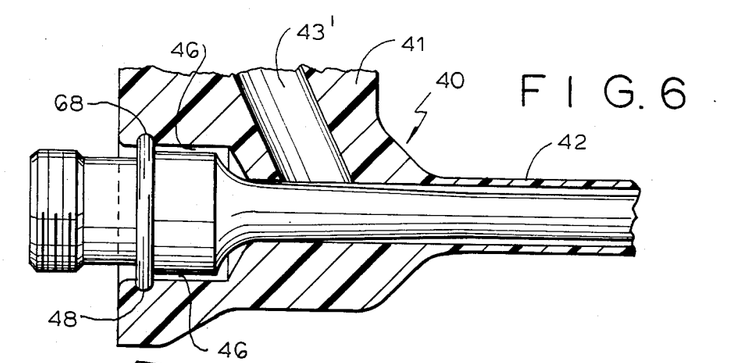
FIG. 6 is a fragmented section of an alternative embodiment of the sealing combination of the needle and sheath means.

Sealing means can be provided on the non-operative end of the reservoir so that it fits cooperatively with the sealing means on the base of the needle, and can be in the form of an continuous annular ring 47 or a continuous annular groove 48 (see FIG. 6). In the case of a continuous annular ring the cross-section can be a dome having a width of from about 0.007 to about 0.025 inches, and preferably from about 0.012 to about 0.018 inches, and a height from about 0.010 to about 0.030 inches, and preferably from about 0.014 to about 0.020 inches, whereas the groove shown in FIG. 6 can have a cross-section with a width of from about 0.006 to about 0.030 inches and preferably from about 0.014 to about 0.022 inches, while the depth of the groove can be from about 0.006 to about 0.030 inches, and is preferably from about 0.012 to about 0.024 inches. In any event, the sleeve and needle are of a dimension such that the sleeve can be elastically fit or "snapped" into place and will remain fixed thereon in a sealing fit so that fluid will not pass therefrom nor will the sheath move from the needle. In order to achieve this it is believed that the interior surface of the sheath sealing means, i.e., the inner surface of the annular ring on the bottom of the groove when they are formed on the sheath, should have a diameter of from about 0.070 to about 0.130 inches, and preferably from about 0.090 to about 0.100 inches while the sealing means on the needle can have a diameter of from about 0.040 to about 0.120, and preferably from about 0.075 to about 0.080 inches, that is to say the diameter of the circle defined by the outer surface of the annular ring or the bottom of the groove when they are formed on the needle.

Finally, with reference to the sleeve there can be seen a housing 41 and a bore 43 that meets the rear part of the sleeve conduit or the reservoir at an angle of from about 45° to about 90° degrees, and has an enlarged section 98 for receipt of fluid passage tube therein. Since the fluid passage conduit can be a normal polyethylene or silicone rubber tube normally used in delivery of biological fluids, the diameter of the connecting aperture can be from about 0.125 to about 0.142 inches in diameter. Furthermore, the fluid passage means 20 can be either permanently attached by gluing or fusion, or can be removably attached as the need may arise.

Figure 7:
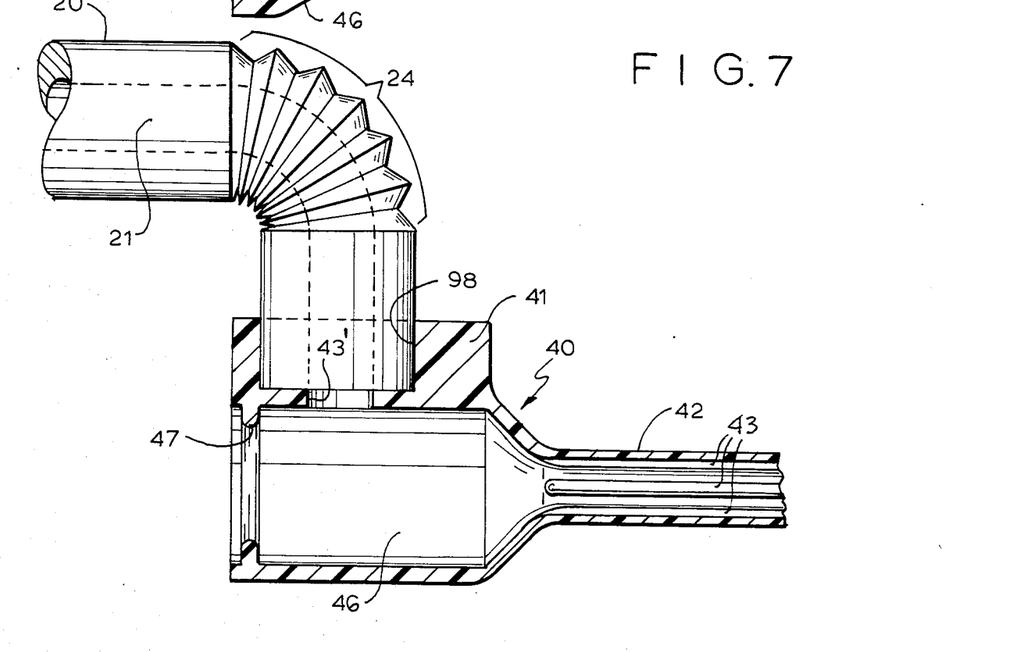
FIG. 7 is a fragmented section of an alternate embodiment of the fluid delivery/withdrawal tube as it is connected to the sheath means.

In order to facilitate fabrication of the sleeve and to accommodate various types of systems, the bore can meet the sleeve conduit at different angles. For example, when the fluid passage tube is a solid-walled tube 20', the angle is preferably from about 58 to about 62 degrees, and most preferably about 60 degrees. In order to provide a 90 degree angle junction between the bore and the sleeve conduit a delivery tube 20'' can be provided with a serated outer surface 24 to relieve outside surface tension on the tube and to reduce deformity of the interior passage 21 of the tube as a result therefrom.

A fluid supply means may include a container or reservoir 75 of the intravenous type that is being suspended from a support 76. In operation treatment fluid such as a saline solution can be continuously fed to the sleeve by the gentle pressure of gravity flow so that the sleeve means is always provided with a continuous supply of fluid. During periods of aspiration, the fluid at the operative site is reduced in volume, but as a result of the fluid "well head" built up in the reservoir, treatment fluid is immediately provided to the sleeve so that there is no resulting void in the treatment fluid which can lead to eye structure collapse, etc.

Method of the Present Invention

In use of the instrument of the present invention, suitable drugs are adminstered to dilate the iris to its maximum extent so that a small incision can be made in the transparant cornea as far as possible from the center of the pupil area. This incision can be made initially only about 1 to 3 millimeters in length to provide access for a knife to enter the anterior chamber for removal of the anterior capsule. In the past after the capsule had been removed, it was necessary that the incision be enlarged to 2 to 12 millimeters, usually 4 to 6 millimeters to provide proper access for the operative tip of the vibratory needle and removal of the fragmented mass. However, the present invention permits both mass size reduction and piece removal without increasing the size of the incision.

After the capsule is removed with a surgical instrument, the operative tip is inserted into the body of the cataract, whereby the lens tissue mass is broken apart into minute particles. During this portion of the operation, as well as others, a supply of treatment fluid is flowing continuously through the sleeve while the transducer is energized periodically for ver short intervals of time.

As the procedure of cataract removal takes place the treatment fluid from the treatment fluid supply enters the work site to keep the eye inflated, by gravity feed. Although the fluid has been described as delivered through the sheath, it may be so delivered by the operating needle and the tissue mass aspiration may be provided through the sheath. However, the first embodiment is believed to be the preferred embodiment. Accordingly, the treatment fluid is supplied from the reservoir of chemical solutions such as saline solution of appropriate type and acts to keep the anterior chamber hydrautically inflated as well as to provide a washing fluid and dispersion fluid at the reduction site.

In order to remove the reduced tissue mass the treatment fluid along with particles of mass can be aspirated through the tip of the vibratory needle, and in the event that the entire mass has been reduced sufficiently, one of the flat end needles can be used in this operation in order to prevent any possible injury to the eye structure.

The practitioner will realize many different advantages and alternative procedures can be employed using the apparatus and method contemplated by the present invention.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. In an apparatus for breaking apart and removing tissue from an enclosed area which includes an elongated instrument capable of being ultrasonically vibrated and having an operative end for placement directly against said tissue, means for applying ultrasonic vibrations, means for supplying treatment fluid in the region adjacent said working tip, and fluid withdrawal means for removing fluid and particles from said enclosed area, said withdrawal means including a conduit extending through said elongated instrument, an improved removable sheath device for delivery of treatment fluid comprising:

sleeve means having a length sufficient to extend substantially the length of said elongated instrument and a transverse cross-section with an inside perimeter greater than the outside perimeter of the transverse cross-section of said instrument whereby fluid introduced to said sleeve means passes between said instrument and said sleeve means, fluid reservoir means in fluid communication with said sleeve means, said reservoir means having a volume for providing a supply of fluid by gravity continuously through said sleeve means, fluid delivery means connected for fluid communication with one of said sleeve means and said fluid reservoir, said delivery means having an external port for connection with said means for supplying treatment fluid, and sealing means which fits cooperatively with said elongated instrument to prevent passage of fluid from the non-operative end of said instrument, whereby said sheath means is sealingly fitted to said instrument so that treatment fluid continuously supplied to said sheath device by gravity is maintained at said operative end substantially in the absence of interruption in flow.

2. The device of claim 1 wherein said fluid withdrawal means further comprises an external reservoir having a source of reduced pressure whereby fluid at said operative end of said instrument is made to flow toward said reservoir.

3. The device of claim 1 wherein said instrument is vibrated at ultrasonic range of from about 5,000 to about 50,000 cycles per second.

4. The device of claim 3 wherein said vibration is about 27,000 cycles per second.

5. The device of claim 1 wherein said instrument is vibrated laterally so that said operative end makes an elliptical pattern.

6. The device of claim 1 wherein said instrument is a titanium needle for removing unwanted tissue material from an animal.

7. The device of claim 1 wherein said sleeve means has a wall thickness of from about 0.001 to about 0.009 inches.

8. The device of claim 10 wherein said wall thickness is about 0.004 inches.

9. The device of claim 1 wherein said sleeve means has a transverse cross-section with an interior perimeter from about 0.002 to about 0.016 inches greater than the exterior perimeter of the transverse cross-section of said instrument.

10. The device of claim 9 wherein said distance is from about 0.004 to about 0.006 inches.

11. The device of claim 9 wherein the wall of said sleeve has a circular transverse cross-section with an inside diameter of from about 0.048 to about 0.068 inches and an outside diameter of from about 0.060 to about 0.080 inches.

12. The device of claim 1 wherein the wall of said sleeve means is tapered at the end which is proximal to the operative end of said instrument.

13. The device of claim 1 wherein said sleeve means comprises at least one opening through the wall of said sleeve at a position proximal the operative end of said instrument whereby fluid provided through said sleeve means is diffused as it passes out said sleeve means.

14. The device of claim 13 wherein there are two said openings.

15. The device of claim 7 wherein said sleeve means further comprises reinforcement means whereby said wall is prevented from longitudinal collapse in the presence of compressive force.

16. The device of claim 15 wherein said reinforcement means comprises at least one rib means extending longitudinally along the wall of said sleeve means.

17. The device of claim 16 wherein said at least one rib means has a dome cross-section which is from about 0.006 to about 0.012 inches wide at its base and is from about 0.002 to about 0.008 inches in cross-sectional height.

18. The device of claim 16 wherein said at least one rib means is formed on the interior surface of said wall.

19. The device of claim 16 wherein there are four longitudinal rib means.

20. The device of claim 1 wherein said sheath means further comprises fluid reservoir means having a dimension sufficient to hold a volume of fluid at least equal to the volume of fluid held between said instrument and said sleeve means whereby a supply of fluid provided by gravity flow is continuously maintained through said sleeve means.

21. The device of claim 20 wherein said reservoir means comprises an extension of said sleeve means having at least one enlarged transverse cross-section and a length sufficient to hold said volume of fluid.

22. The device of claim 21 wherein said reservoir has two enlarged transverse cross-sections.

23. The device of claim 22 wherein the first said cross-section of said reservoir is substantially circular with a diameter of from about 0.130 to about 0.145 inches and has a length of from about 0.055 to about 0.075 inches and the second said cross-section has a diameter of from about 0.005 to about 0.120 inches and has a length of from about 0.080 to about 0.145.

24. The device of claim 1 wherein said fluid delivery means comprises body means at the non-operative end of said sleeve means, said body means having a fluid delivery bore which extends from said external port and is in fluid communication with one of said sleeve means and said reservoir, and attachment means at said external port for connecting fluid passage tube.

25. The device of claim 21 wherein said bore meets one of said sleeve means and said reservoir at an angle of from about 45° to about 90°.

26. The device of claim 25 wherein said bore has a circular transverse cross-section having a diameter of from about 0.054 to about 0.062 inches.

27. The device of claim 26 wherein said attachment means comprises an enlargement in the cross-section dimension of said bore having a cross-section dimension and shape so that a fluid passage tube is inserted therein.

28. The device of claim 27 wherein the cross-section of said enlargement is circular and has a diameter of from about 0.125 to about 0.142 inches.

29. The device of claim 28 wherein said fluid passage tube is a cylindrical infusion tube having a cross-section with an outer diameter of from about 0.125 to about 0.142 inches.

30. The device of claim 28 wherein said tube is made of a material selected from polyethylene and silicone.

31. The device of claim 29 wherein said fluid passage tube is permanently secured to said attachment means.

32. The device of claim 29 wherein said fluid passage tube is removeably attached to said attachment means.

33. The device of claim 29 wherein said fluid passage tube has a solid wall and said angle at which said bore meets one of said sleeve means and said reservoir is from about 58° to about 62°.

34. The device of claim 29 wherein said angle is 90° and said fluid passage tube has an outer wall with a substantially serrated outside linear surface profile at a point proximal its attachment to said fluid delivery/-withdrawal bore whereby said tube is bent at said point with reduced outer surface tension on said tube and reduced deformity of the interior passage of said tube.

35. The device of claim 34 wherein said wall of said fluid delivery tube is from about 0.024 to about 0.030 inches thick and the depth of the depressions of said serrations are from about 0.010 to about 0.017 inches, and the apexes of said serrations are one of peaks and truncated peaks.

36. The device of claim 35 wherein the pitch of said serration is from about 0.025 to about 0.035 inches.

37. The device of claim 1 wherein said sealing means comprises an extension of said sleeve means at the non-operative end of said sleeve, said extension having an annular seal which provides said cooperative fit with said elongated instrument.

38. The device of claim 21 wherein said sealing means comprises a continuation of said extension of said reservoir means at the non-operative end, said continuation of said extension having an annular seal which provides said cooperative fit.

39. The device of claim 37 wherein said annular seal is a continuous annular ring protruding from the interior surface of the wall of said extension, said ring having a dimension which sealingly fits in an annular groove provided on the nonoperative end of said instrument.

40. The device of claim 39 wherein said annular ring has a dome-shaped cross-section having a width of from about 0.007 to about 0.025 inches and a cross-sectional height from said interior surface of from about 0.010 to about 0.030 inches, and said groove has a cross-sectional width of from about 0.006 to about 0.030 inches and a depth of from about 0.006 to about 0.030 inches.

41. The device of claim 40 wherein said ring width is from about 0.012 to about 0.018 inches and said ring height is from about 0.014 to about 0.020 inches, and said groove width is from about 0.014 to about 0.022 inches and said depth is from about 0.012 to about 0.024 inches.

42. The device of claim 40 wherein the diameter of the circle defined by the inner circumference of the interior surface of said annular ring is from about 0.070 to about 0.130 inches and the diameter of the circle defined by the bottom of said groove is from about 0.040 to about 0.120 inches whereby said ring is sealingly secured in said groove.

43. The device of claim 42 wherein said annular ring diameter is from about 0.090 to about 0.100 inches and said groove diameter is from about 0.075 to about 0.080 inches.

44. The device of claim 37 wherein said annular seal is a continuous annular groove on the interior surface of said extension, said groove having a dimension which sealingly fits over an annular ring provided on the non-operative end of said instrument.

45. The device of claim 44 wherein said annular ring has a dome-shaped cross-section having a width of from about 0.007 to about 0.025 inches and a cross-sectional height from said instrument surface of from about 0.010 to about 0.030 inches, and said groove has a cross-sectional width of from about 0.006 to about 0.030 inches and a cross-sectional depth of from about 0.006 to about 0.030 inches.

46. The device of claim 45 wherein said ring width is from about 0.012 to about 0.018 inches, and said ring height is from about 0.014 to about 0.020 inches, and said groove width is from about 0.014 to about 0.022 inches, and said depth is from about 0.012 to about 0.024 inches.

47. The device of claim 45 wherein the diameter of the circle defined by the bottom of said groove is from about 0.070 to about 0.130 inches, and the diameter of the circle defined by the surface of the outer circumference of said annular ring is from about 0.040 to about 0.120 inches whereby said groove is sealingly secured over said ring.

48. The device of claim 50 hwerein said annular ring diameter is from about 0.090 to about 0.100 inches and said groove diameter is from about 0.075 to about 0.080 inches.

49. The device of claim 1 which is made of synthetic polymeric material.

50. In an apparatus for breaking apart and removing tissue from an enclosed area which includes an elongated instrument capable of being ultrasonically vibrated and having an operative end for placement directly against said tissue, means for applying ultrasonic vibrations, means for supplying treatment fluid in the region adjacent said operative end, and fluid withdrawal means for removing fluid and particles from said enclosed area, said withdrawal means including a conduit extending through said elongated instrument, an improved means for delivery and removal of treatment fluid from said operative end comprising:

a removable sheath device, said removable sheath device comprising;

sleeve means having a length sufficient to extend substantially the length of said elongated instrument and a transverse cross-section with an inside perimeter greater than the outside perimeter of the transverse cross-section of said instrument whereby fluid introduced to said sleeve means passes between said instrument and said sleeve means, fluid reservoir means in fluid communication with said sleeve means, said reservoir means having a volume for providing a supply of fluid by gravity continuously through said sleeve means, fluid delivery means connected for fluid communication with one of said sleeve means and said fluid reservoir, said delivery meanshaving an external port for connection with a supply of treatment fluid, and sealing means which fits cooperatively with said elongated instrument to prevent passage of fluid from the non-operative end of said instrument; and an improved needle for use as said elongated instrument comprising;

an elongated barrel means having an operative end and a non-operative end, said conduit extending the length thereof with an inlet port at the operative end, base means provided at said non-operative end of said barrel means, said conduit continuing from said barrel through said base means with an outlet port at the non-operative end of said base means, said base means further comprising means for connecting said needle to said means for supplying ultrasonic vibrations, and mounting means for sealingly mounting said sheath device on said needle, whereby said sheath means is sealingly fitted to said needle so that treatment fluid continuously supplied to said sheath device by gravity is maintained at said operative end substantially in the absence of interruption in flow.

51. The combination instrument of claim 50 which further comprises a source of vibratory motion which imparts ultrasonic vibrations to said needle in a lateral direction so that the path of the end of said needle is elliptical.

52. The combination instrument of claim 50 which further comprises a fluid conducting tube connected at said external port and a fluid conducting tube connected at said connecting conduit of said needle base means whereby fluid is delivered to and withdrawn from said sheath and said needle.

53. The combination of claim 52 wherein said tube connected to said external port of said sheath is provided with a continuous flow of treatment fluid, and said tube connected to said connecting conduit of said needle base is attached to a source of negative pressure whereby fluid present at the operative end of said needle is aspirated through said conduit of said barrel means.

* * * * *

UNITED STATES PATENT AND TRADEMARK OFFICE
CERTIFICATE OF CORRECTION

PATENT NO. : 4,634,420

DATED : January 6, 1987

INVENTOR(S) : Spinosa, et al.

It is certified that error appears in the above-identified patent and that said Letters Patent are hereby corrected as shown below:

At Column 16, Line 2 and 3,

"fluid delivery/-withdrawal bore" should read --fluid delivery bore--.

Signed and Sealed this

Thirty-first Day of March, 1987

Attest:

DONALD J. QUIGG

Attesting Officer

Commissioner of Patents and Trademarks